United States Patent [19]
Pelleg

[11] Patent Number: 5,874,420
[45] Date of Patent: Feb. 23, 1999

[54] PROCESS FOR REGULATING VAGAL TONE

[75] Inventor: Amir Pelleg, Haverford, Pa.

[73] Assignee: Allegheny University of the Health Sciences, Philadelphia, Pa.

[21] Appl. No.: 771,518

[22] Filed: Dec. 23, 1996

Related U.S. Application Data

[60] Provisional application No. 60/009,228, Dec. 26, 1995.

[51] Int. Cl.$^6$ .................................................. A61K 31/675
[52] U.S. Cl. ................................................. 514/81; 514/89
[58] Field of Search ........................................ 514/89, 81

[56] References Cited

U.S. PATENT DOCUMENTS

| | | | |
|---|---|---|---|
| 4,673,563 | 6/1987 | Berne et al. | 424/9 |
| 5,049,372 | 9/1991 | Rapaport | 424/1.1 |
| 5,219,841 | 6/1993 | Inaba et al. | 514/47 |
| 5,504,090 | 4/1996 | Neely | 514/263 |

OTHER PUBLICATIONS

Abbrachio et al., "Purinoceptors: Are There Families of P2X and P2Y Purinoceptors?", *Pharmacol. Ther.*, 1994, 64, 445–475.

Amour et al., "Responsiveness of in situ canine nodose ganglion afferent neurones to epicardial mechanical or chemical stimuli", *Cardiovasc. Res.*, 1994, 28, 1218–1225.

Belhassen et al., "A Comparative Study of the Electrophysiologic Effects of Striadyne, Adenosine Triphosphate and Adenosine in the Canine Heart", *Cardiology*, 1985, 72, 113–122.

Belhassen et al., "Electrophysiologic Effects of Adenosine Triphosphate and Adensine on the Mammalian Heart: Clinical and Experimental Aspects", *J. Am. Coll. Cardiol.*, 1984, 4(2), 414–424.

Belhassen et al., "Comparative clinical and electrophysiologic effects of adenosine triphosphate and verapamil on paroxysmal reciprocating junctional tachycardia", *Circulation*, 1988, 77(4), 795–805.

Belhassen et al., "Electrophysiologic effects of adenosine–5'–triphosphate on atrioventricular reentrant tachycardia", *Circulation*, 1983, 68(4), 827–833.

Benedini et al., "Value of purinic compounds in assessing sinus node dysfunction in man: A new diagnostic method", *European Heart J.*, 1984, 5, 394–403.

Cardenas et al., "Efecto Del Acido Adenosintrifosforico Sobre Las Propiedades Fisiologicas Del Corazon", *Arch. Inst. Cardiol. Mex.*, 1964, 34, 485–494 (English Summary provided).

Emmelin et al., "Systemic Effects of Adenosine Triphosphate", *Br. J. Pharmacol. Chemotherap.*, 1948, 3, 273–284.

Fukunaga et al., "Intravenous ATP Attenuates Surgical Stress Responses and Reduces Inhalation Anesthetic Requirements in Humans", *Anesthesiology*, 1990, 73(A400).

Hugues et al., "Etude De L'Action Chronotrope De L'ATP Chez L'Homme", *Coeur Med. Inter.*, 1980, 19, 227–234 (English Summary provided).

Hurt et al., "Electrophysiological–anatomic correlates of ATP–triggered vagal reflex in dogs. II. Vagal afferent traffic", *Am. J. Physiol.*, 1994, 267, H1093–H1097.

Kobayashi et al., "Adenosine Triphosphate–Sensitive Ventricular Tachycardia in Man", *Eur. J.C.P.E.*, 1994, 4(1), 11–19.

Li et al., "Effect of Adenosine or Adenosine Triphosphate on Antidromic Tachycardia", *JACC*, 1994, 24(3), 728–731.

Moro et al., "Dose related efficacy of adenosine triphosphate in spontaneous supraventricular tachyarrhythmias", *Int. J. Cardiol.*, 1989, 25, 207–212.

Pelleg et al., "Electrophysiological Effects of Adenosine–Tri–Phosphate and Adenosine on the Canine Heart", *Fed. Proc.*, 1983, 42, 731, No. 2571.

Pelleg et al., "Comparative Electrophysiologic Effects of Adenosine Triphosphate and Adenosine in the Canine Heart: Influence of Atropine, Propanolol, Vagotomy, Dipyridamole and Aminophylline", *Am. J. Cardiol.*, 1985, 55, 571–576.

Pelleg et al., "Evidence for Vagal Involvement in the Electrophysiologic Actions of Exogenous Adenosine and Adenosine Triphosphate in the Canine Heart", *J. Auton. Pharmac.*, 1985, 5, 207–212.

Pelleg et al., "Evidence Against Prostaglandin Mediation of the Differential Electrophysiologic Effects of ATP Versus Adenosine in the Canine Heart", *J. Cardio. Pharm.*, 1986, 8, 534–538.

Pelleg et al., "Role of the vagus in modulation by $Ca^{2+}$ of the depressant action of adenosine and adenosine 5'–triphosphate on the canine sinus node in vivo," *J. Auton. Pharmac.*, 1987, 7, 127–134.

Pelleg et al., "Electrophysiologic–anatomic correlates of ATP–triggered vagal reflex in dogs", *Am. J. Physiol.*, 1993, 265, H681–H690.

Pelleg et al., "Mechanism of action of ATP on canine pulmonary vagal C fibre nerve terminals", *J. Physiol.*, 1996, 490.1, 265–275.

Rankin et al., "Adenosine or adenosine triphosphate for supraventricular tachycardias? Comparative double–blind randomized study in patients with spontaneous or inducible arrhythmias", *Am. Heart J.*, 1990, 119(2), 316–323.

Remington's Pharmaceutical Sciences, 18th Ed., Gennaro Alphonso (ed.), Mack Publishing Company, Easton, PA, 1990.

Rinne et al., "Comparative effects of adenosine triphosphate on accessory pathway and atrioventricular nodal conduction", *Am. Heart J.*, 1988, 115(5), 1042–1047.

Rossi et al., "Modification par les nucleotides adenyliques de l'effet chronotrope de la stimulation du vague sur le coeur de rat", *CR Soc. Biol.*, 1967, 161, 860–861.

(List continued on next page.)

*Primary Examiner*—William R. A. Jarvis
*Attorney, Agent, or Firm*—Seidel, Gonda, Lavorgna & Monaco, PC

[57] ABSTRACT

The present invention provides methods of altering vagal tone in a patient by administering a therapeutically effective amount of a mediator of $P_{2x}$-purinoceptors located on vagal afferent nerve terminals to the patient. Diagnostic applications are also provided.

10 Claims, 3 Drawing Sheets

OTHER PUBLICATIONS

Saito et al., "Intravenous Injection of Adenosine Triphosphate for Assessing Sinus Node Dysfunction in Patients with Sick Sinus Syndrome", *Arzneim–Forsch/Drug Res.,* 1993, 43, 1313–1316.

Sharma et al., "Disparate Effects of Adenosine Triphosphate on Sinus Node Automaticity and AV Nodal Conduction in Man", *JACC,* 1987, 9, 246A.

Sharma et al., "Comparative Quantitative Electrophysiologic Effects of Adenosine Triphosphate on the Sinus Node and Atrioventricular Node", *Am. J. Cardiol.,* 1988, 61, 330–335.

Sharma et al., "Intravenous Adenosine Triphosphate during Wide QRS Complex Tachycardia: Safety, Therapeutic Efficacy, and Diagnostic Utility", *Am. J. Med.,* 1990, 88, 337–343.

Sharma et al., "Negative Chronotropic Effects of Adenosine Triphosphate on the Sinus Node are Mediated by Muscarinic Cholingeric and not Purinergic Receptors", *JACC,* 1988, 11(2), 227A.

Trezise et al., "Effects of divalent cations on the potency of ATP and related agonists in the rat isolated vagus nerve: implications for $P_2$ purinoceptor classification", *Br. J. Pharmacol.,* 1994, 113, 463–470.

Trezise et al., "Characterization of purinoceptors mediating depolarization of rat isolated vagus nerve", *Br. J. Pharmacol.,* 1993, 110, 1055–1060.

Viskin et al., "Clinical and Electrophysiologic Effects of Magnesium Sulfate on Paroxysmal Supraventricular Tachycardia and Comparison with Adenosine Triphosphate", *Am. J. Cardiol.,* 1992, 70, 879–885.

Viskin et al., "Acute management of paroxysmal atrioventricular junctional reentrant supraventricular tachycardia: Pharmacologic strategies", *Am. Heart. J.,* 1990, 120, 180–188.

Wayne et al., "The Effect of Adenosine Triphosphate on the Electrocardiogram of Man and Animals", *Br. Heart J.,* 1949, 11, 55–67.

Katchanov, et al., "Intracoronary ATP Triggers a Vagus Nerve Dependent Cardiac Depressor Reflex in the Canine Heart", *Circulation* 94: I–489 (Nov. 1, 1996).

Katchanov, et al., "Electrophysiological–anatomic correlates of ATP–triggered vagal reflex in the dog. III. Roles of cardiac afferents" *Am. J. Physiol.* 270 (Heart Circ. Physiol. 39); H1785–H1790 (1996).

Pelleg & Hurt, "Adenosine 5'–Triphosphate Induces Chemosensitive Pulmonary–Cardiac Depressor Reflex", *Circulation* 86:I–637, abstr #2534 (1992).

Control

ATP

PROCESS FOR REGULATING VAGAL TONE

CROSS REFERENCE TO RELATED APPLICATION

This application claims the benefit of U.S. Provisional Application No. 60/009,228 filed Dec. 26, 1995.

FIELD OF THE INVENTION

The present invention relates to methods of regulating vagal tone in human patients.

BACKGROUND OF THE INVENTION

The parasympathetic limb, i.e., the vagus nerve, is a major component of the autonomic nervous system which regulates the function of various organs and tissues throughout the body. Sensory stimuli elicit neural signals (i.e.,action potentials) traveling in the vagus nerve via afferent fibers to the central nervous system which in turn sends neural signals to effector organs via efferent vagal fibers; known as vagal reflexes. In addition, sensory stimuli can elicit localized release of biologically active compounds (i.e., neuropeptides) from afferent nerve terminals, independent of afferent traffic traveling to the central nervous system; known as axonal reflexes. The vagus nerve maintains a basal level of activity, evidenced by the output of the efferent vagal fibers, or tone. Vagal tone is increased or decreased depending upon the body's needs, generally in response to internal or external sensory stimuli. The former can be either central or peripheral. The effects of the vagus nerve are mediated by the neurotransmitter acetylcholine, released from efferent nerve terminals, activating muscarinic cholinergic receptors on target cells.

Alteration of vagal tone is used in humans in the acute management of pathophysiologic conditions and therapy of certain diseases. For example, certain cardiac pathologies are associated with vagally mediated slowing of the heart rate (i.e., bradyarrhythmias). This slowing can hemodynamically compromise a patient's welfare. Also, there is considerable evidence that vagal reflexes and vagal afferent axonal reflexes contribute to the pathophysiology and symptomatology of asthma and other obstructive pulmonary diseases.

Existing approaches for alteration of vagal tone are based on pharmacologic modulation of the function of the vagal efferent fibers. For instance, vagal tone can be modulated by blockade of muscarinic cholinergic receptors as well as by the inhibition of acetylcholinesterase, an enzyme which degrades acetylcholine. Indeed, anticholinergic drugs are very effective in the treatment of bradyarrhythmias associated with acute myocardial ischemia. These drugs are also effective bronchodilators in chronic obstructive pulmonary diseases. However, there is presently no therapeutic approach which targets the axonal reflexes which exacerbate certain pathophysiologic conditions such as asthmatic bronchoconstriction.

The number of people in the United States and other developed countries suffering from asthma has doubled over the last twenty years. The cost of illness related to asthma in the United States was estimated to be 6.2 billion dollars in 1990. Today, it is estimated that 10% of the world's population suffers from asthma. Furthermore, the number of asthma deaths worldwide continues to increase. This trend in increasing mortality due to asthma is paradoxical in view of the decreased mortality from other diseases and our better understanding of the pathophysiology of asthma. This situation is probably due, at least in part, to the lack of new therapeutic modalities including those which also target the neural component of the disease.

The vagus nerve also mediates neurogenic human fainting (i.e., vasovagal syncope). A vasovagal reaction is characterized by an inappropriate decrease in blood pressure and/or heart rate. Patients suspected of suffering from vasovagal syncope are subjected to a clinical test (i.e., tilt test) in which the induction of fainting is attempted by head-up tilt in the presence or absence of drugs (e.g., isoproterenol). This is a tedious and expensive test. Furthermore, there is presently no diagnostic procedure available to determine the severity of this pathology quantitatively.

Adenosine 5'-triphosphate (ATP) is a purine nucleotide found in every cell of the human body where it plays a major role in cellular metabolism and energetics. Once outside of cells, however, ATP exerts different effects on various tissues and organs. The actions of extracellular ATP are known to be mediated by specific cell surface receptors, $P_2$-purinoceptors. These receptors are subdivided into two families: $P_{2x}$ and $P_{2y}$ (Abbracchio and Burnstock, *Pharmacol Ther.* (1994) 64, 445–475). Classification is based upon certain aspects of the signal transduction initiated by the activation of these receptors as well as the relative agonist potencies of ATP and ATP analogues in different systems. For example $P_{2x}$-purinoceptor-mediated responses are characterized by the order of agonist potencies of $\alpha$, $\beta$-methylene ATP which is greater than $\beta$, $\gamma$-methylene ATP which is greater than ATP and 2methyl-thio ATP (those two being equal). Thus, it has been recognized that purinoceptors are unique and their stimulation activates specific mechanisms. Extracellular ATP is known to affect neural elements via the activation of a $P_{2x}$-purinoceptor.

Trezise et al., *Br. J. Pharmacol.*(1993) 110, 1055–1060, have shown that ATP can depolarize rat vagal fibers in vitro and that this action is mediated by $P_{2x}$- purinoceptors.

However, such findings are not applicable to the autonomic nervous system of humans for a number of reasons. First, tests with single cells do not address the problems of purine metabolism associated with whole tissue. Further, it is uncertain whether tissues in vitro express the same receptor types as in vivo. In addition, work performed with ATP in rats can not be extrapolated to humans because rats lack certain specific type of afferent/efferent reflex loops triggered by ATP which are found only in cats, dogs and humans.

ATP has been employed as a therapeutic in human patients. For example, ATP has been used for many years in the acute management of paroxysmal supraventricular tachycardia. However, it is believed that the mechanism of ATP's action in this setting involves the degradation of ATP to adenosine and the action of adenosine on the specialized tissue of the heart (i.e., atrio-ventricular node). Indeed, the use of adenosine in this setting is the subject of Belardinelli et al., U.S. Pat. No. 4,673,563. ATP has also been shown to be effective against cancer in animal models and in humans. However, the mechanism of action of ATP in this setting involves the immune system and/or direct action on tumor cells and is independent of the autonomic nervous system. The use of ATP as anti-cancer therapy is the subject of Rapaport, U.S. Pat. No. 5,049,372.

The present invention provides a unique approach to modulating vagal tone and vagal axonal reflexes in humans through the activation and blockade of $P_2$-purinoceptors on afferent vagal nerve terminals in vivo.

SUMMARY OF THE INVENTION

In some aspects of the present invention are provided methods of altering vagal tone in mammals suffering from conditions associated with undesirable vagal tone comprising administering a mediator of $P_{2x}$-purinoceptors on afferent nerve terminals.

In other aspects of the present invention are provided diagnostic methods of detecting undesirable propensity for acute increase in vagal tone by administering a mediator to a patient and measuring the patient's vagal reflex triggered by the said mediator as compared to a standard reflex.

These and other aspects of the invention will be described in greater detail below.

DETAILED DESCRIPTION OF THE PRESENT INVENTION

In accordance with the present invention is provided a novel approach to modulating vagal tone of the autonomic nervous system. Treatment of conditions associated with the parasympathetic limb of the autonomic nervous system generally has focused on the modulation of the efferent portion of the vagal system. The present invention is based upon the novel approach of modulating afferent nerve traffic which in turn ultimately evokes a modulated response of efferent fibers. The modulated reflex may be cardio-cardiac or pulmonary-pulmonary.

Figure 1:
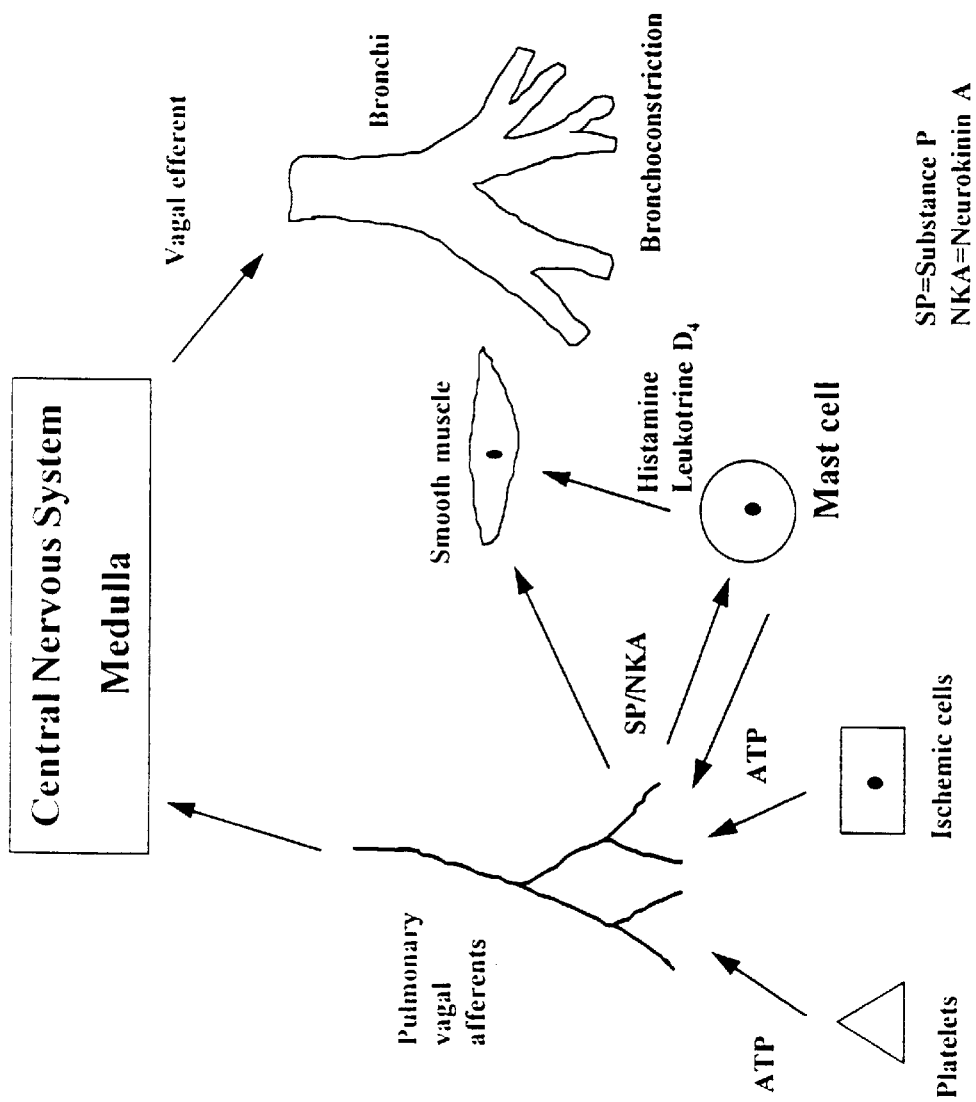
FIG. 1 is a schematic representation of the pulmonary-pulmonary and axonal reflexes which is a subject of the invention.

The cardio-cardiac reflex involves afferent traffic elicited in the left ventricle of the heart which travels to the brain where it is subjected to central processing. The outcome of the central processing is efferent neural traffic which reaches the heart to cause slowing of heart rate and reduced force of cardiac muscle contraction. The pulmonary—pulmonary reflex consists similarly of afferent and efferent traffics as well as central processing, however, the efferent traffic of this reflex reaches the lungs to cause bronchoconstriction. FIG. 1 illustrates the pulmonary—pulmonary reflex. In both reflexes the efferent nerve terminals release acetylcholine which acts on target cells; i.e., it slows heart rate or causes the bronchia of the lungs to constrict. These reflexes are protective mechanisms of the body, the cardio-cardiac reflex reduces the work load of the heart and thereby reduces oxygen demand. The pulmonary—pulmonary reflex protects the lungs by limiting the amount of noxious material entering the lungs. In the same fashion that patients receive drugs to lower their body temperature, elevation of which is a protective mechanism against bacterial infection, there is a need under specific pathophysiologic conditions to modulate the cardio-cardiac and pulmonary—pulmonary reflexes.

In further aspects of the invention, a patient's vagal reflexes may be modulated and the extent of the response observed. In accordance with this embodiment, efferent nerve traffic is observed and compared with standard efferent nerve traffic associated with normal vagal function. Deviation from standard, i.e., normal vagal response will serve to aid the clinician in determining the severity of a patients condition and indicate an appropriate treatment. A standard vagal response is that of a healthy human subjects. As would be appreciated by those skilled in the art, a standard response might be obtained by measuring vagal reflex of healthy patients in response to a selected mediator.

The vagus nerve has also been implicated in the pathophysiology of the acute phase of pulmonary embolism. The mechanism of enhanced vagal tone in this setting was not known. However, in accordance with the present invention it is believed that ATP released from activated platelets in the lungs activates $P_2$-purinoceptors located on vagal afferent nerve terminals thereby triggering a pulmonary—pulmonary vagal reflex. This reflex causes bronchoconstriction and bronchial secretion. Both, bronchoconstriction and mucous plug in bronchi, commonly found in patients at the time of pulmonary embolism, contribute to the causes of death in this setting.

In further aspects of the invention, vagal reflexes elicited during the acute phase of pulmonary embolism may be suppressed by an antagonist mediator administered to the patient.

In accordance with the present invention vagal tone is modulated by the administration of one or more mediators. Mediators effective for purposes of this invention, act upon $P_2$-purinoceptors on afferent nerve terminals. In preferred methods of the present invention, the purinoceptor is $P_{2x}$-purinoceptor. Administration of one or more mediator is preferably by specifically targeted administration. For instance, localized catheters may be used to effectively administer the mediator to the desired target.

Mediation may increase or decrease vagal tone. Where vagal tone is insufficient, an agonist mediator should be administered. Agonists of the present invention include, but are not limited to agonists at $P_{2x}$-purinoceptors such as ATP and its analogues. Thus, for example, where a patient suffers from state-post myocardial infarction, high vagal tone might be desired as a cardioprotective measure, an agonist such as ATP may be administered in accordance with the present invention. Alternatively, an antagonist may be administered when vagal tone is too high; and/or to suppress axonal reflexes. For instance, patients suffering from asthma or other obstructive airway diseases, would benefit from methods of the present invention. In accordance with such methods, an antagonist of the $P_{2x}$-purinoceptor such as pyridoxalphosphate-6-azophenyl-2', 4'-disulphonic acid may be administered to decrease vagal tone.

In accordance with the present invention, mediators of the present invention may be administered in therapeutically effective amounts in accordance with methods appreciated by those skilled in the art.

The mode of administration of mediators according to the method that is the invention includes any means that produces contact of the active ingredient with the agent's site of action in the body of a mammal or in a body fluid or tissue. These modes of administration include but not limited to oral, topical, hypodermal, intravenous, intramuscular and intraparenteral methods of administration. In some preferred embodiments of the invention, the mediator is administered by a catheter directed to the site of the afferent nerve terminals. In practicing the method that is the invention, the mediators may be administered singly or in combination with other compounds used in the method that is the invention, other pharmaceutical compounds are preferably administered with a pharmaceutically acceptable carrier selected on the basis of the selected route of administration and standard pharmaceutical practice.

The method may include administration of compounds to mammals, preferably humans, in therapeutically effective amounts. The dosage administered in any particular instance will depend upon factors such as the pharmacodynamic characteristics of the compound of the invention, its mode and route of administration; age, health, and weight of the recipient; nature and extent of symptoms; kind of concurrent treatment, frequency of treatment, and the effect desired.

It is contemplated that the daily dosage of a compound used in the method that is the invention will be in the range of from about 1 µg to about 100 mg per kg of body weight, preferable from about 10 µg to about 20 mg per kg per day. Pharmaceutical compositions may be administered in a single dosage, divided dosages or in sustained release. Persons of ordinary skill will be able to determine dosage forms and amounts with only routine experimentation based upon the considerations of this invention.

The method of administering mediators include administration as a pharmaceutical composition parenterally in sterile liquid dosage forms or topically in a carrier. The mediators may be formulated into dosage forms according to standard practices in the field of pharmaceutical preparations. See Gennaro Alphonso, ed., *Remington's Pharmaceutical Sciences*, 18th Ed., (1990) Mack Publishing Company, Easton, Pa.

For parenteral administration, mediators may be mixed with a suitable carrier or diluent such as water, a oil, saline solution, aqueous dextrose (glucose), and related sugar solutions, and a glycol such as propylene glycol or polyethylene glycol. Solutions for parenteral administration contain preferably a water soluble salt of the compound. Stabilizing agents, antioxidizing agents and preservatives may also be added. Suitable sulfite, and ascorbic acid, citric acid and its salts, and sodium EDTA. Suitable preservatives include benzalkonium chloride, methyl- or propyl-paraben, and chlorbutanol.

The following examples are illustrative and are not meant to be limiting of the present invention.

EXAMPLES

Experiments were performed as described in Pelleg and Hurt, *J. Physiol.* (1996) 490.1, 265–275, which is incorporated by reference herein in its entirety. Experiments were performed on anaesthetized (sodium pentobarbitone, 30 mg $kg^{-1}$ plus 3 mg $kg^{-1}$, $h^{-1}$ I.V.) dogs (17.0±0.6kg; either sex) artificially ventilated with room air using a respirator. The physiological range for arterial blood pH, $P_{O2}$ and $P_{CO2}$ (7.32–7.42, 85–110 mmHg, and 28–41 mmHg, respectively) was maintained by adjustment of the respirator rate and tidal volume as well as by supplemented $O_2$. Body temperature was maintained with a heating mattress (rectal temperature range, 36.2°–37.2° C.). Systemic arterial blood pressure was determined with a Millar pressure transducer located in the descending aorta. A peripheral vein was cannulated for the administration of a physiological saline solution and maintenance doses of the anaesthetic. Catheters were introduced via the right femoral vein and left atrial appendage and positioned in the right atrium and left atrium, respectively, for the administration of test solutions. For intrapulmonary administration of drugs and test compounds, a Swan-Ganz catheter was introduced via a femoral vein and positioned in the distal portion of the right pulmonary artery. The chest was opened by a longitudinal sternotomy. The right cervical vagosympathetic trunk was exposed by a midcervical longitudinal section of the skin and careful dissection of neck muscles and connective tissues. The edges of the cut skin were elevated and secured to create a trough which was filled with warm (37° C.) mineral oil. A section of the vagosympathetic trunk was placed on a small plate of black Perspex and fine branches were separated from the main bundle by careful dissection using microsurgical tools and a dissecting microscope (Model F212, Jenopik Jena, GmbH, Germany).

Extracellular neural action potentials were recorded using a custom-made bipolar electrode, which consisted of two platinum-iridium wires (1.25×0.0125cm), connected to a high-impedance first-stage differential amplifier (model AC8331, CWE Inc., Ardmore, Pa., USA) via a shielded cable. The output of the first-stage amplifier was fed into a second-stage differential amplifier (model BMA-831/C, CWE, Inc.) Isolated fibres were laid on the pair of platinum wires. Vagal C fibres with chemosensitive endings have a sparse irregular discharge which is never associated with cardiac or respiratory cycles. Confirmation of fibre type was obtained by: first, monitoring the response to capsaicin (10 µg $kg^{-1}$, intra-right atrial bolus); second, monitoring the response to mechanical stimulation of the lungs using gentle probing with forceps as well as inflation of the lungs to 2–3 times the tidal volume; and third, determining the speed of conduction using a stimulating electrode positioned distal to the initial recording site.

A subgroup of animals was treated with PTX (30 µg $kg^{-1}$, given into a peripheral vein of conscious animals) 48 h prior to experimentation. (PTX was donated by Dr. E. Hewlett, University of Virginia, Charlottesville, Va., USA.) Animals did not show any signs of distress during that period. These animals were subjected to glucose tolerance tests prior to and 48 h after PTX administration to confirm PTX intoxication. The test consisted of the application of a bolus of dextrose (1.1 g $kg^{-1}$,I.V.) and subsequent withdrawal of blood samples (5 ml, every 10 min). Glucose and insulin levels in the blood samples withdrawn during these tests were determined by the Diagnostic Laboratory at Cornell University, New York State College of Veterinary Medicine, Ithaca, N.Y., USA.

Purine compounds (ATP, adenosine 5'-diphosphate (ADP), adenosine 5'-monophosphate (AMP) and adenosine; 3–6 µmol $kg^{-1}$ and capsaicin (10 µg $kg^{-1}$) were given as a rapid bolus into the right atrium (5 ml test solution+5 ml physiological saline flush) or the right pulmonary artery (1 ml test solution+3 ml physiological saline flush). When given in the latter site, smaller doses were used, i.e. 0.5–3 µmol $kg^{-1}$ for purine compounds and 1–5 µg $kg^{-1}$ for capsaicin. α,β-Methylene ATP (α,β-mATP) and β,γ-methylene ATP (β,γ-mATP) were give as one low dose only (0.75 µmol $kg^{-1}$) to avoid systemic side effects. Volume controls consisted of either 5+5 ml or 1+3 ml physiological saline. All injections were performed in the same mode by the same person. To exclude involvement of baroreceptors in the recorded neural activity, the latter was monitored before and after a bolus of nitroglycerine (1mg, I.V.; n=5). The effect of ganglionic transmission blockade on the effects of ATP and capsaicin was determined by the administration of hexamethonium (10 mg $kg^{-1}$, I.V.; n=7).

To determine the purinoceptor subtype which mediates the action of ATP on pulmonary vagal nerve terminals, ATP and capsaicin were given prior to (control) and following the administration of either the selective $P_{2x}$-purinoceptor antagonist pyridoxal phosphate-6-azophenyl-2', 4'-disulphonic acid (PPADS; 15 mg $kg^{-1}$, I.V.; 2.5–5.0 mg $kg^{-1}$. intrapulmonary artery; n=6) or the selective $P_{2x}$-purinoceptor antagonist, Reactive Blue 2 (RB2, Cibacron Blue 3GA, Sigma; 7.7 mg $kg^{-1}$, I.V.; n=4).

At the end of the experiments animals were killed using sodium pentobarbitone (100 mg kg$^{-1}$, I.V.) plus 3M KCl (10 ml, I.V.)

Results are expressed as means±S.E.M.

Example 1
Patterns of the actions of capsaicin and ATP and ATP Analogues

In anaesthetized dogs with a stable sinus rhythm, a sinus cycle length of 443±25 ms and mean systemic arterial blood pressure of 89±6 mmHg, the right atrial administration of capsaicin (10 µg kg$^{-1}$) induced a burst of action potentials in right cervical vagal fibres, which was associated with transient slowing of the heart rate and a drop in arterial blood pressure. Similar responses were recorded in forty-six fibres in thirty-eight dogs. The administration of ATP caused similar effects, i.e. a burst of action potentials in the same fibres, a transient prolongation of sinus cycle length and a drop in systemic arterial blood pressure (i.e., capsaicin and ATP maximally reduced blood pressure 20±4 and 58±3%, respectively). The time-to-peak negative chronotropic effect of ATP was significantly shorter than the time-to-peak vasodilatory effect. The elapsed times from the moment of injection of capsaicin and ATP to the beginning of the neural bursts and the duration of the elicited bursts were similar. Much smaller amounts of ATP (0.5–3 µmol kg$^{-1}$) and capsaicin (1–5 µg kg$^{-1}$) given into the right pulmonary artery elicited similar neural activity to that observed following right atrial administration of those compounds. The degradation products of ATP, ADP, AMP and adenosine, did not excite the fibres (n=30) that were excited by ATP and capsaicin.

Example 2
Characterization of the nerve fibres excited by ATP

The fibres were otherwise quiescent with no activity associated with either heart rate or respiration cycle. Mechanical stimulation of the right lung elicited a burst of action potentials in the fibres. Elevation of tracheal pressure due to lung inflation to 2–3 times its tidal volume excited the fibres. Intra-left atrial administration of ATP failed to excite the fibres indicating that their terminals were not in the heart and/or the bronchi. The time to burst of neural action potentials following right atrial ATP and capsaicin (latency) was short, about 3 s, thus excluding activation of bronchial fibres. The conduction velocity of the fibres was slow (0.85±0.13 ms$^{-1}$; range, 0.54–1.58; n=7), within the range of velocities established for canine pulmonary C fibres.

Example 3
Effect of nitroglycerine

The drop in systolic arterial blood pressure produced by nitroglycerine (1 mg, I.V.), from 104±12 to 77±8 mmHg (26±6%; P<0.05; n=5); did not elicit any specific activity in the fibres in which bursts of action potentials were elicited by capsaicin and ATP.

Example 4
Effects of hexamethonium

Treatment with the ganglionic blocker hexamethonium (10 mg kg$^{-1}$, I.V.; n=7) did not alter the afferent traffic elicted by either capsaicin or ATP, but markedly attenuated the negative chronotropic actions of the two compounds. The drop in systemic arterial blood pressure caused by capsaicin was also abolished by hexamethonium. In contrast, hexamethonium did not alter the effect of ATP on blood pressure.

The fact that hexamethonium did not alter the transient reduction of blood pressure caused by ATP and the significantly larger time-to-peak effect of ATP on blood pressure versus that of capsaicin indicates that a non-neural factor, i.e. adenosine, the product of the enzymatic degradation of ATP, is mediating, to a large extent, the peripheral vasodilatory action of ATP.

Example 5
ATP signal transduction at pulmonary C fibre terminals

Since neither ADP, AMP nor adenosine (equimolar doses given in the same mode as ATP) induced action potentials in any of the fibres tested, it was hypothesized that P$_2$-purinoceptors were mediating the action of ATP. To test this hypothesis several pharmacological agents were used.

First, the partially degradable analogue of ATP, β, γ-mATP (0.75 µmol kg$^{-1}$) did not elicit neural action potentials in any of the fibres studied (5 fibres in 5 dogs). In contrast, α,β-mATP (0.75 µmol kg$^{-1}$), did elicit bursts of action potentials in these fibres (n=7), which were followed by extended periods (2–5 min) of increased activity in comparison with the pre-α, β-mATP conditions.

Second, the selective P$_2$,-purinoceptor antagonist PPADS markedly attenuated the number of bursts elicited by ATP in pulmonary vagal C fibres (n=6). Intra-right pulmonary administration of PPADS reduced the number of neural action potentials elicited by intra-right pulmonary administration of ATP in a time-dependent manner. In contrast PPADS did not affect the neural response to intra-right pulmonary-applied capsaicin.

Third, the P$_{2y}$-purinoceptor antagonist RB2 did not affect the actions of either ATP or capsaicin on vagal pulmonary afferent C fibres (n=4).

Thus, while ATP and capsaicin stimlate the same afferent fibers, the differential potency and the response of two compounds to the P2-purinoceptor antagonist PPADS suggest that different receptors mediate their actions.

Examples 1–5 show that an intra-right atrial bolus of ATP elicited a transient burst of action potentials in cervical vagal fibers; similar activity was elicited by capsaicin, given in the same mode; neural activity was elicited in otherwise quiescent slow-conducting fibers; adenosine, AMP, or ADP did not elicit this activity; α,β-mATP was much more potent than ATP while β, γ-mATP was inactive; PPADS but not RB2 abolished this action of ATP; and neither PTX nor hexamethonium prevented this action of ATP.

Example 6
ATP stimulates pulmonary vagal afferent C fiber terminals by activating P$_{2x}$-purinoceptors.

The fact that adenosine, AMP and ADP, unlike ATP, did not elicit neural responses (Example 1) indicates that the action of ATP was mediated by a P2-purinoceptor. Furthermore, the structure-function cascade: α, β-mATP >>ATP >>β, γ-mATP as shown in Example 5 strongly suggests that the P$_2$-purinoceptor activated by ATP was that of the P$_{2x}$ subtype. This is supported by the data obtained with the P$_2$-purinoceptor antagonists. (Example 5) Specifically, PPADS, a P$_2$-purinoceptor antagonist, but not RB2, a P$_{2y}$-purinoceptor antagonist effectively blocked the action of ATP on the pulmonary vagal afferent C fiber nerve terminals.

Example 7
ATP-triggered bronchoconstriction in the dog

Figure 2A:
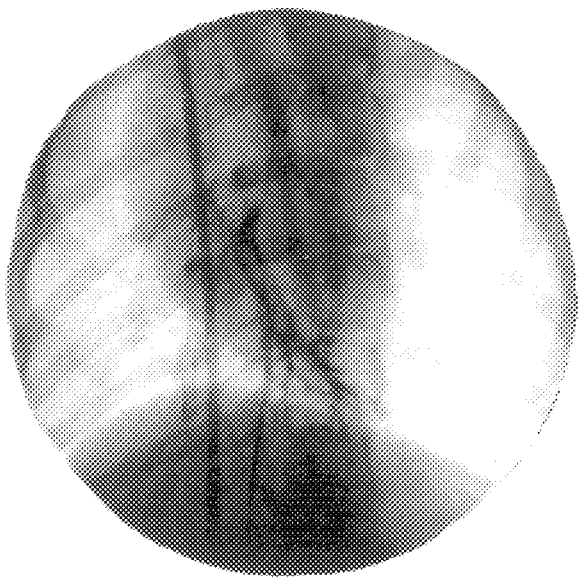
FIG. 2 (A and B) is a bronchogram of a control (baseline conditions) (FIG. 2A) and a bronchogram (FIG. 2B) showing the pronounced bronchoconstriction induced by administration of ATP (FIG. 2B).

ATP (8 µmol/kg) was given as a rapid bolus into the right atrium of the anesthetized dog heart. A bronchogram was obtained eight seconds later using tantalum powder and digital fluoroscopy. FIG. 2 is a bronchogram of a control (baseline conditions) (FIG. 2A) and a bronchogram (FIG.

Figure 2B:
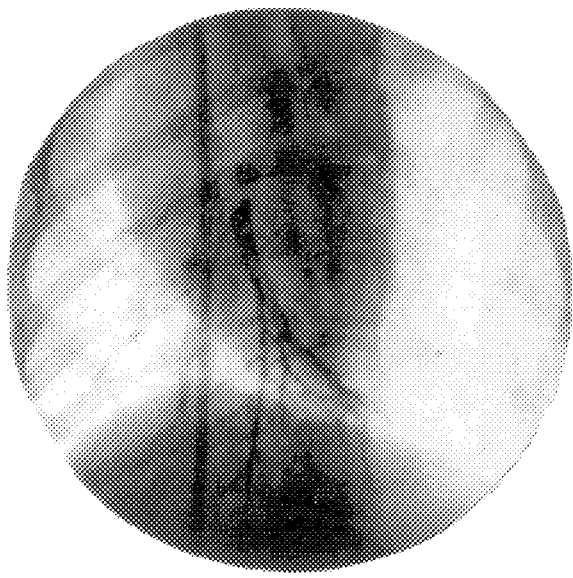

2B) showing the pronounced bronchoconstriction induced by administration of ATP (FIG. 2B). The effect of ATP was transient and all monitored parameters returned to baseline values within 120 seconds.

Example 8
Effects of ATP on respiratory air flow

Figure 3:
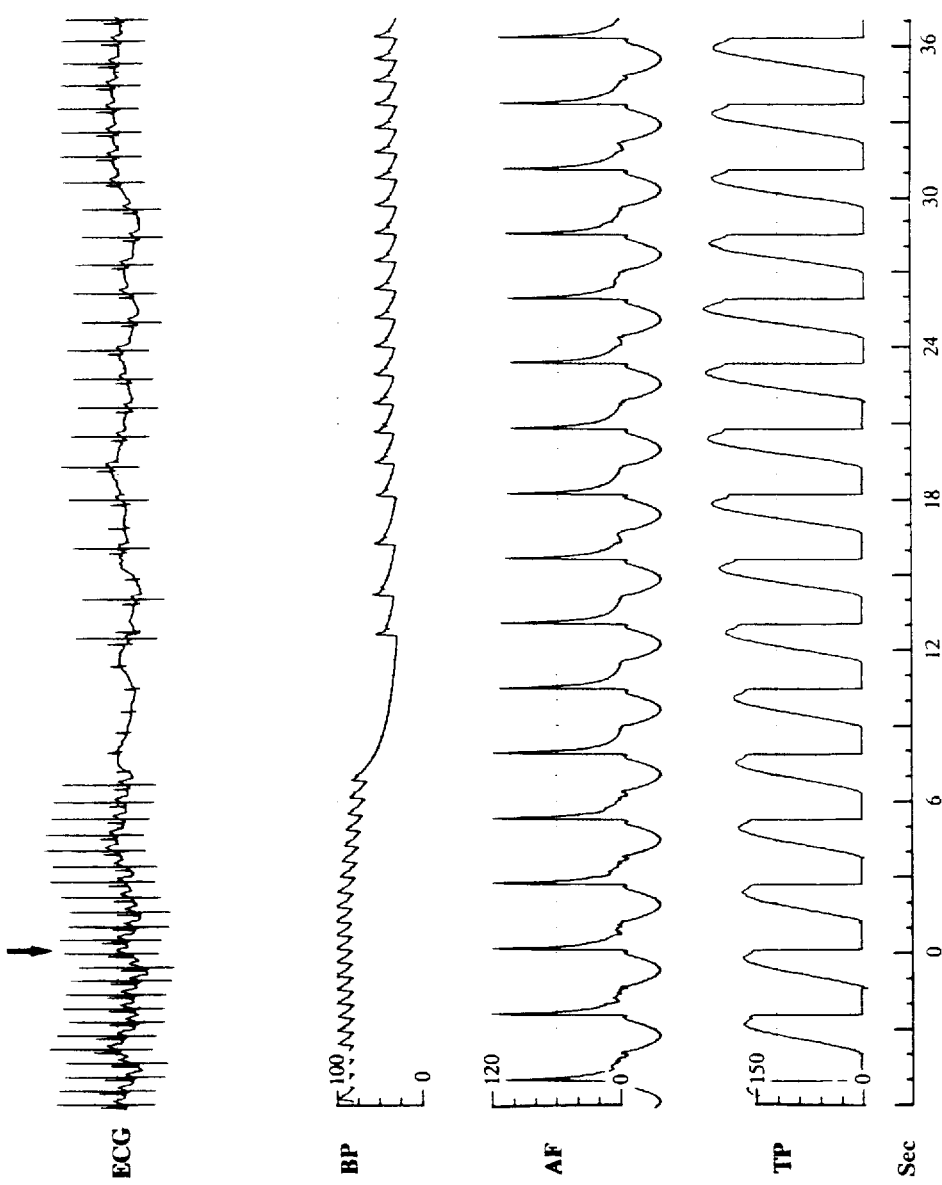
FIG. 3 is shows an (A) electrocardiogram (ECG) of (B) systemic arterial blood pressure (BP, mmHg), (C) pulmonary air flow (AF, 1/min) and (D) tracheal pressure (TP, mmH$_2$O) of a dog following administration of ATP (marked by the arrow, sec-0)

ATP (8 μmol/kg) was given as a rapid bolus into the right atrium of the anesthetized dog heart. FIG. 3 shows the electrocardiogram (ECG) systemic arterial blood pressure (BP, mmHg) pulmonary air flow (AF, 1/min) and tracheal pressure (TP, mmH$_2$O) of the dog following administration of ATP (marked by the arrow, sec-0). As evidenced by FIG. 3, ATP exerted pronounced negative chronotropic and dromotropic effects on sinus node automaticity and AV nodal conduction, reduced BP and AF and increased TP. All of the effects were transient and markedly attenuated by bilateral cervical vagotomy (not shown).

Example 9
Effects of ATP on cardiac/cardiac reflex

Equimolar doses (0.5, 1.0 μmol/kg) of ATP and aenosine were given as rapid boluses into the left main (LM), circumflex (Cfx), and left anterior descending (LAD) coronary arteries in anaesthetized, closed chest dogs (n=5), before and after bilateral cervical vagotomy. Percent maximal prolongation of sinus cycle length (%ΔSCL) and time peak effect (tp) were determined. %ΔSCL and $t_p$ were 220±62% and 2.1±0.3 sec, and 14±5% and 7.4±1.3 sec for ATP and adenosine, respectively (p<0.01). Bilateral cervical vagotomy either abolished or markedly attenuated the effect of ATP; in the latter case there was no difference between the effects of ATP and adenosine and their $t_p$ was similar. The site-potency cascade for ATP was LM>>Cfx>LAD. Thus, ATP triggers a vagal reflex by stimulating vagal afferent nerve terminals in the left ventricle. This reflex mediates the negative chronotropic action of ATP and is independent of adenosine, the product of its enzymatic degradation.

What is claimed is:

1. A method of modulating vagal tone in a mammal suffering from a condition associated with undesirable vagal tone comprising administering a therapeutically effective amount of a mediator of $P_{2x}$-purinoceptors located on vagal afferent nerve terminals.

2. The method of claim 1 wherein the mediator is selected from the group consisting of antagonists, agonists and receptor allosteric modifiers.

3. The method of claim 2 wherein the antagonist is pyridoxyalphosphate-6-azophenyl-2'4'-disulphonic acid.

4. The method of claim 2 wherein the agonist is ATP.

5. The method of claim 1 wherein the condition is asthma.

6. The method of claim 1 wherein the condition is state-post myocardial infarction.

7. The method of claim 1 wherein the condition is pulmonary embolism.

8. The method of claim 1 wherein the condition is bradyarrhythmia.

9. A method of diagnosing abnormal vagal tone in a mammal comprising administering a mediator to $P_{2x}$-purinoceptors located on afferent nerve terminals of a patient and measuring the patient's vagal reflex elicited by said mediator as compared to a standard reflex whereby reflex which varies from standard reflex is indicative of abnormal vagal function.

10. The method of claim 9 wherein the abnormal vagal tone is associated with vasovagal syncope.

* * * * *